United States Patent
Friedel et al.

(10) Patent No.: US 9,598,316 B2
(45) Date of Patent: *Mar. 21, 2017

(54) SOLUTION COMPRISING ORGANOFUNCTIONAL ALKALI SILICONATES, SILICATES AND METHOD OF PRODUCTION THEREOF

(75) Inventors: Manuel Friedel, Zürich (CH);
Spomenko Ljesic, Rheinfelden (DE);
Christian Waβmer, Hausen (DE);
Susanne Zölitz, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 367 days.

This patent is subject to a terminal disclaimer.

(21) Appl. No.: 14/111,185

(22) PCT Filed: Feb. 27, 2012

(86) PCT No.: PCT/EP2012/053263
§ 371 (c)(1),
(2), (4) Date: May 22, 2014

(87) PCT Pub. No.: WO2012/139803
PCT Pub. Date: Oct. 18, 2012

(65) Prior Publication Data
US 2014/0374656 A1    Dec. 25, 2014

(30) Foreign Application Priority Data

Apr. 11, 2011 (DE) .................. 10 2011 007 137

(51) Int. Cl.
*C04B 24/42* (2006.01)
*C07F 7/18* (2006.01)
(Continued)

(52) U.S. Cl.
CPC .......... *C04B 24/42* (2013.01); *B01J 19/0006* (2013.01); *C07F 7/188* (2013.01); *C08L 83/04* (2013.01); *C08G 77/24* (2013.01)

(58) Field of Classification Search
CPC ........ C04B 24/42; B01J 19/0006; C07F 7/188
See application file for complete search history.

(56) References Cited

U.S. PATENT DOCUMENTS

| | | |
|---|---|---|
| 4,252,569 A | 2/1981 | Roedel |
| 5,282,998 A | 2/1994 | Horn et al. |

(Continued)

FOREIGN PATENT DOCUMENTS

| | | |
|---|---|---|
| JP | 49-014535 A | 2/1974 |
| WO | WO 02/083808 A2 | 10/2002 |

(Continued)

OTHER PUBLICATIONS

U.S. Appl. No. 14/110,840, filed Oct. 9, 2013, Friedel, et al.
(Continued)

*Primary Examiner* — Kaj K Olsen
*Assistant Examiner* — Alexander Polyansky
(74) *Attorney, Agent, or Firm* — Oblon, McClelland, Maier & Neustadt, L.L.P.

(57) ABSTRACT

The invention relates to a method for producing a solution comprising organofunctional siliconates, silicates and, optionally, the cocondensation products thereof, and to the solutions and an installation for the production thereof.

16 Claims, 2 Drawing Sheets

(51) Int. Cl.
*C08L 83/04* (2006.01)
*B01J 19/00* (2006.01)
*C08G 77/24* (2006.01)

(56) References Cited

U.S. PATENT DOCUMENTS

| | | |
|---|---|---|
| 5,932,757 A | 8/1999 | Standke et al. |
| 6,685,766 B2 | 2/2004 | Standke et al. |
| 6,767,982 B2 | 7/2004 | Standke et al. |
| 6,770,327 B2 | 8/2004 | Edelmann et al. |
| 6,780,955 B2 | 8/2004 | Barfurth et al. |
| 6,841,197 B2 | 1/2005 | Standke et al. |
| 7,939,616 B2 | 5/2011 | Barfurth et al. |
| 8,147,918 B2 | 4/2012 | Standke et al. |
| 8,394,885 B2 | 3/2013 | Friedel et al. |
| 8,481,654 B2 | 7/2013 | Edelmann et al. |
| 8,679,247 B2 | 3/2014 | Friedel et al. |
| 2003/0021904 A1 | 1/2003 | Hirsbrunner et al. |
| 2008/0261024 A1* | 10/2008 | Xenopoulos et al. ........ 428/331 |
| 2011/0308423 A1 | 12/2011 | Friedel et al. |
| 2013/0040058 A1 | 2/2013 | Friedel et al. |
| 2013/0085210 A1 | 4/2013 | Friedel et al. |
| 2013/0087080 A1 | 4/2013 | Friedel et al. |
| 2013/0092052 A1 | 4/2013 | Friedel et al. |
| 2013/0284071 A1 | 10/2013 | Friedel et al. |

FOREIGN PATENT DOCUMENTS

| | | |
|---|---|---|
| WO | WO 02/083808 A3 | 10/2002 |
| WO | WO 2012/084401 A1 | 6/2012 |
| WO | WO 2012/139803 A1 | 10/2012 |
| WO | WO 2012/139804 A1 | 10/2012 |
| WO | WO 2013/072185 A1 | 5/2013 |

OTHER PUBLICATIONS

International Search Report issued Apr. 24, 2012 in PCT/EP2012/053263.
U.S. Appl. No. 14/358,437, filed May 15, 2014, Ljesic, et al.
U.S. Appl. No. 14/629,177, filed Feb. 23, 2015, Studte, et al.

* cited by examiner

SOLUTION COMPRISING ORGANOFUNCTIONAL ALKALI SILICONATES, SILICATES AND METHOD OF PRODUCTION THEREOF

The invention relates to a method of production of a solution comprising organofunctional alkali siliconates, silicates and optionally co-condensation products thereof, and to the solutions themselves and to a plant for preparation thereof.

Owing to water absorption by porous mineral building materials, such as concrete, sandstones, lime sandstones, gypsum, ceramics or fired clay products, for example bricks, in the presence of water or moisture, the building materials may be damaged. Repair of building materials damaged in this way is very laborious and expensive. Incorporation of hydrophobizing agents on the surface or in the bulk during production of these building materials, in order to prevent water absorption and consequent damage of the building materials, is known. For some time, siliconates have played an important role as hydrophobizing agents, especially when less alkaline building materials, such as clay products, are to be treated.

EP 0 650 968 discloses a two-stage process for continuous production of alkali alkylsiliconates from alkyltrichlorosilanes via alkyltrialkoxysilanes. U.S. Pat. No. 4,281,147 describes a method of production of aqueous alkali organylsiliconates by reaction of organylalkoxypolysiloxanes with NaOH or KOH. EP 15366 relates to a method of production of alkali chloride-free alkali methylsiliconates by reaction of alkali trichlorosilanes with a base, precipitation of the intermediate by acidification and final dissolution of the washed filter cake in base. DE 3 220 393 describes guanidinium organylsiliconates and -silicates and a method of production from organyltrialkoxysilanes and guanidinium hydroxide. U.S. Pat. No. 4,252,569 discloses a method of production of sodium methylsiliconates by reaction of sodium methyltrichlorosilanes with a methanol/water mixture in a first step, after which the reaction products are put into aqueous sodium hydroxide solution. The main drawback of the method described is the need for phase separation after the first reaction step. WO 02/083808 discloses the hydrophobizing action of mixtures of 20 ml water, a defined amount of 28% potassium methylsiliconate and/or technical sodium silicate (waterglass) with 28% $SiO_2$, which are prepared by mixing and are dried onto sand immediately at 60° C.

Neither a composition comprising organofunctional alkali siliconates, silicates and co-condensates thereof, nor a technical method for the industrial production of said composition, are known from the prior art.

LIST OF REFERENCE SYMBOLS SHOWN IN FIG. 1 AND FIG. 2

0 plant
1 metering device
1.1 feed pipe
1.2 control device
1.3 first vessel
1.4 gas feed pipe
1.5 feed pipe
2 device with delivery means
2.1 second vessel
2.2 delivery means, in particular delivery tube/hose
2.3 end of delivery means
2.4 collecting device
2.5 gas feed pipe
3 lumen
4 SOLUTION
5 step 2 reactor
6 feed pipe (inert gas)
7 step 1 reactor
8 feed pipe (educts).

The problem to be solved by the present invention is therefore to provide an economical method of production of organofunctional alkali siliconate solutions, containing a silicate fraction, and optionally co-condensation products thereof, suitable for hydrophobizing impregnation of mineral building materials, in particular of surfaces of mineral building materials and/or hydrophobizing thereof in the bulk during manufacture. Preferably, porous mineral building materials and/or subsoils are impregnated with the solutions according to the invention. Another problem was to provide stable solutions of the compounds, preferably with a high content of these compounds. A further problem was to provide a plant for performing the method according to the invention.

The problem was solved by the method according to the present invention, the solution according to the invention comprising organofunctional alkali siliconates, silicates and optionally co-condensation products thereof and by the plant according to the present invention. Further features and combinations thereof are explained in detail in the description.

It has surprisingly been found that it is possible to prepare solutions of organic alkali siliconates, silicates and co-condensation products thereof if the preparation is effected in the presence of inert gas. A solution preferably means a homogeneous mixture, in particular comprising organofunctional alkali siliconates, silicates and optionally co-condensation products thereof (together solutes) and at least one solvent, wherein the solutes are preferably dissolved completely in the solvent, i.e. the solution is preferably clear.

Surprisingly, it was also found that alkylsiliconate solutions with a silicate fraction can be prepared by reacting mixtures of alkyltrichlorosilanes and tetrachlorosilane in the desired ratio in a step 1 with ethanol or a water/ethanol mixture. The mixture obtained, the reaction product, can be introduced in step 2 into an aqueous lye, preferably an aqueous NaOH or KOH solution. Moreover, it is preferable if the solution is such that after introduction of the mixture the desired final concentration of alkylsiliconate and silicate is obtained. Furthermore, it is preferable if the introduction of the mixture into the solution is carried out in such a way as to ensure that no solid deposits form, in particular of a silicate type. Moreover, the alcohol or a water/alcohol mixture can be used up to 1 to 100 mol. %, in particular 10 to 100 mol. % relative to the hydrolysable residues Si-Hal of compounds I and II, in particular ethanol is used as alcohol. Furthermore, it may be preferable to use a sub-stoichiometric amount of alcohol, such as EtOH or a water/alcohol mixture, such as water/EtOH, in particular 5 to 99 mol. %, preferably 10 to 95 mol. %, especially preferably 20 to 90 mol. %, in particular about 80 mol. %, in each case relative to the molar amount of the hydrolysable Si-Hal bonds or hydrolysable Hal residues on silicon atoms, preferably of general formulae I and II.

Surprisingly it was found that this takes place reliably if the mixture from step 1, the reaction product, is injected by means of a continuous $N_2$ stream into the initial charge of aqueous lye, i.e. the mixture is distributed immediately in the solution. Moreover, this distribution of the mixture by the combined use of intensive stirring and injection using inert gas is particularly efficient. The formation of solid silicate particles or deposits can be avoided particularly well. If required, the hydrolysis alcohol can be removed from the solution obtained and/or further diluted with water. Generally, the alcohol-containing solution obtained is ready for use and is suitable for application.

The two-stage process according to the invention for preparing solutions of alkylsiliconates and silicates in aqueous solution comprises a first reaction step, in which a mixture of alkyldichloro- and/or trichlorosilanes and tetrachlorosilane is reacted with a water/ethanol mixture or pure ethanol, and the reaction product obtained is injected, in a second step, by means of an inert gas stream, in particular an $N_2$ gas stream into an aqueous lye, preferably an aqueous alkali hydroxide solution, in a way that prevents the formation of solid deposits, in particular of a silicate type. Moreover, it may be preferable to use a sub-stoichiometric amount of EtOH or water/EtOH mixture, relative to the molar amount of hydrolysable Si-Hal bonds.

The invention relates to a two-stage method of preparing solutions comprising organofunctional alkali siliconates, silicates and optionally co-condensation products thereof and optionally a content of alcohol, which are prepared in the presence of an inert gas, in particular solutions comprising alkali propylsiliconates, silicates and co-condensation products thereof and solutions obtainable by this method.

The invention also relates to a method of preparing a solution comprising organofunctional alkali siliconates, silicates and optionally co-condensation products thereof, and solutions obtainable by this method, comprising the steps of:
1) preparing a mixture comprising at least one organofunctional silane of general formula I, at least one halosilane of formula II and alcohol, in which
    at least one organofunctional silane of general formula I $$(R^1)_x SiHal_{(y-x)} \quad (I)$$

with $R^1$ independently an organofunctional residue, in particular an organofunctional residue which comprises in each case independently 1 to 18 carbon atoms, preferably in each case independently a linear, branched or cyclic alkyl radical having 1 to 18 carbon atoms, better n-propyl, or alternatively having 6 to 16 carbon atoms, and with Hal as hydrolysable residue, wherein Hal is independently chlorine or bromine, preferably chlorine, and with x equal to 1 or 2 and with y=4, preferably x=1 and
   at least one halosilane of formula II $$Si(Hal)_4 \quad (II)$$

with Hal as hydrolysable residue, wherein Hal denotes independently chlorine or bromine, preferably Hal denotes chlorine, and
   at least one alcohol and optionally water are reacted, in particular an alcohol-water mixture, in particular the alcohol comprises ethanol, methanol, propanol, such as iso-propanol or n-propanol, or mixtures with at least two of the alcohols;

2) introducing the reacted mixture from step 1 in the presence of inert gas, preferably under inert gas, into an aqueous alkali hydroxide solution, preferably an aqueous NaOH and/or KOH solution; wherein the inert gas is supplied, in the process, in such a way that it introduces the mixture from step 1 a little at a time, preferably dropwise, directly into the aqueous alkaline solution, in particular injects it into the solution or distributes the mixture from step 1 in the solution, especially preferably the mixture from step 1 is distributed homogeneously in the solution, wherein it is further preferred that the mixture in step 1 and/or the solution in step 2 are stirred vigorously. Preferably the mixture in step 1 is prepared while stirring vigorously and is also directly incorporated and distributed in the solution in step 2 while stirring vigorously in the presence of an inert gas. Anchor, propeller, cross-jaw, impeller and/or disk stirrers can preferably be used. Furthermore, flow disturbers can be used advantageously. The alcohol used in step 1 is, according to the invention, in the mixture from step 1, also introduced in the second process step into the aqueous alkali hydroxide solution. In contrast to methods of the prior art, separation is not necessary, but can take place optionally after introduction into the aqueous alkali hydroxide solution, e.g. by distillation.

According to the invention, a solution comprising organofunctional alkali siliconates, silicates and optionally co-condensation products thereof is obtained in step 2, wherein the organofunctional groups of the siliconate independently correspond to $R^1$ as defined above and below. $R^1$ is especially preferably independently n-propyl, isopropyl, n-butyl, isobutyl, n-hexyl, n-octyl, isooctyl, cyclohexyl. i-Butyl is in particular a 2-methyl-propyl and i-octyl is a 2,3,4-trimethylpentyl.

Alkali hydroxide means both alkaline-earth and alkali hydroxides. These are in particular but not exhaustively: lithium hydroxide, sodium hydroxide, potassium hydroxide, magnesium hydroxide, calcium hydroxide, barium hydroxide, which can also be present in mixtures or together with other alkaline, water-soluble salts or compounds.

The inert gas can be a gas or carrier gas, with the proviso that it must not react with the educts or products, in particular it must not react with the alkaline solution. Therefore carbon dioxide is not suitable as inert gas. The inert gas preferably comprises nitrogen and/or argon and other gases that do not react with the mixtures and/or solutions. This is for example propane etc. thus, in general, solvents can also be evaporated, such as n-pentane or other vaporizable solvents known by a person skilled in the art. Generally, however, incombustible and ecologically compatible gases are preferred.

The organofunctional radical $R^1$ of the general formula (I) each independently comprises a radical having 1 to 18 carbon atoms, and especially in each case independently corresponds to a linear, branched or cyclic alkyl radical having 1 to 18 carbon atoms, an alkylene radical having 1 to 18 carbon atoms, an aryl radical having 6, 10, 12 or 13 carbon atoms, or an alkylaryl or arylalkyl radical having 7 to 18 carbon atoms, $R^1$ preferably being an alkyl radical having 2 to 16 carbon atoms, $R^1$ more preferably being an alkyl radical having 3 to 16 carbon atoms, better having 3 to 5 carbon atoms or 6 to 16 carbon atoms. Particularly preferred radicals $R^1$ are n-propyl, i-propyl, n-butyl, i-butyl or else n-pentyl, preference being given according to an alternative also to long-chain alkyl groups having 6 to 16 carbon atoms, such as n-hexyl, cyclohexyl or octyl, in which case preference is given to a certain content of alcohol in the solution for solubilization of the long-chain alkyl group. The organofunctional radicals $R^1$ mentioned then also form the organofunctional radicals in the organofunctional alkali siliconates and their co-condensates with silicates.

Preferred organofunctional silanes of general formula I are alkylhalosilanes, such as an alkyltrihalosilane, dialkyldihalosilane, such as preferably alkyltrichlorosilane, dialkyldichlorosilane. Further preferred are propyltrihalosilane, dipropyldihalosilane, in particular propyltrichlorosilane, dihexyldichlorosilane, hexyltrichlorosilane, cyclohexyltrihalosilane, such as cyclohexyltrichlorosilane, octyltrihalosilane, such as octyltrichlorosilane to mention just a few, wherein a person skilled in the art also knows and can use the corresponding brominated or mixed-halogenated alkylhalosilanes, in particular comprising chlorine and bromine.

According to the method according to the invention it is preferable if the organofunctional silane of general formula I and the halosilane of formula II are added, in particular are made available, in step 1 in a molar ratio from 0.5:10 to 10:0.5, preferably in a ratio from 1:10 to 10:1, wherein a ratio of about 1:1 to 9:1 is especially preferred. According to the invention, a ratio of silane of formula I to halosilane of formula II of about 1:1 is used, in particular with a variation of plus/minus 0.5.

Moreover, alternatively or additionally to the aforementioned features, it is preferable if the alcohol; in particular ethanol, methanol, propanol, such as iso-propanol or n-propanol, or mixtures with at least two of the alcohols; is added in step 1 in a ratio from 1 to 100 mol. % relative to the hydrolysable residues, i.e. relative to the total of Hal (halogen atoms in I and II), in particular of chlorine atoms, in mol in general formulae I and II. Thus, if there are approx. 2 mol of chlorine atoms in total in the mixture comprising silanes of formula I and II, then preferably about 0.2 to 2 mol of alcohol, such as preferably ethanol, is added. Preferably 1 to 100 mol. % ethanol relative to the total of chlorine atoms in mol, preferably 5 to 99 mol. %, especially preferably 10 to 95 mol. %, quite especially preferably 20 to 90 mol. %, in particular about 80 mol. %, is added to an alkyltrichlorosilane and tetrachlorosilane, which are present in a ratio from 10:5 to 10:5.

A special feature of the method is that the mixture from step 1 is introduced directly in step 2 into an aqueous, alkaline solution and is converted to a solution comprising organofunctional siliconates, silicates and optionally co-condensation products thereof, in particular the mixture from step 1 is injected a little at a time, preferably dropwise by means of inert gas directly into the solution or is distributed directly in the solution, i.e. the mixture from step 1 is introduced or injected under the surface of the solution, preferably it is strongly distributed directly. An especially efficient distribution of the solution introduced a little at a time, in particular dropwise, is achieved with a combination of pneumatic distribution, i.e. by the inert gas, and mechanical distribution, such as stirring.

The molar ratio of hydrolysable residues of the mixture from step 1 to the alkali hydroxide used is as a rule between 1:5 to 5:1, preferably it is between 1:3 to 3:1, especially preferably about 1:2 to 2:1, or also about 1:1 with a variation of plus/minus 0.5. Thus, for about 1 mol hydrolysable residues about 2 mol alkali hydroxide can be used or according to an alternative procedure also for about 2 mol hydrolysable groups about 1 mol alkali hydroxide. During addition to the alkali hydroxide solution, the hydrolysable residues comprise the Hal residues and/or the alkoxy groups formed by esterification with the alcohol, in particular on the silanes of general formulae I and/or II as well as optionally on the formed organofunctional alkali siliconates, silicates and optionally formed co-condensation products thereof.

The alcohol in the solution; in particular ethanol, methanol, propanol, such as iso-propanol or n-propanol, or mixtures with at least two of the alcohols; wherein the solution comprises organofunctional alkali siliconates, silicates and optionally co-condensation products thereof, can optionally be removed. This can preferably take place by distillation. Preferably, it is not necessary for the alcohol to be removed from the solution since the solution is immediately ready for use and if required can easily be diluted further with water.

In general, the solution, in particular the alcohol-containing solution, can be adjusted directly during production to a content of organofunctional alkali siliconates, alkali silicates and optionally co-condensation products thereof from 1 to 40 wt. % and all values in between—it is immediately ready for use—preferably it can be adjusted to a content from 1 to 30 wt. %, alternatively to 7 to 40 wt. %, especially preferably to 7 to 30 wt. % or also about 8 to 28 wt. %. Using the method according to the invention it is therefore possible to prepare highly concentrated solutions which are also stable, preferably for 12 months. If required the solution can be diluted, i.e. a purely aqueous or an alcoholic solution, with water to a content of organofunctional alkali siliconates, alkali silicates and optionally co-condensation products thereof from 1 to 40 wt. % and to any values in between, preferably to 1 to 30 wt. %, or alternatively to 7 to 40 wt. %, especially preferably to 7 to 30 wt. % or also about 8 to 28 wt. %.

The content is also related directly to the mineral building material used and/or the type of application. Thus, for application on surfaces, solutions with a low content may be suitable, and for example for hydrophobization in the bulk, solutions with a high content, especially for hydrophobization of gypsum-containing mineral building materials. Highly concentrated solutions may also be preferable if water is already added as mixing water for hydrophobization in the bulk. In general the content of active substance can also be between 1 to 10 wt. % in the solution, or depending on the application 1 to 5 wt. %, 5 to 10 wt. %, 10 to 15 wt. %, 15 to 20 wt. % or 20 to 30 wt. % or also 30 to 40 wt. %.

During preparation of the mixture of organofunctional silane of formula I, the halosilane of formula II and alcohol or alcohol/water mixture, the reaction causes the temperature to rise in step 1. According to the method, the temperature in step 1 should not exceed 80° C., especially preferably the temperature should not exceed 60° C., and cooling is used if necessary. Reaction also causes the temperature to rise in step 2, but it should not exceed 80° C., preferably should not exceed 60° C., i.e. cooling is used if necessary in step 2 or the mixture from step 1 is introduced more slowly, a little at a time into the alkaline solution.

On introduction of the mixture from step 1 into the alkali hydroxide solution there can be formation of the organofunctional alkali siliconates, such as $MO[Si(R^1)_xY_{(y-2)-x}O]_a M$ of the idealized formula III or $MO[Si(R^1)_xO^-_{(y-2)-x}O]_a M+M_a$ of the idealized formula IIIa, alkali silicates, such as $MO[Si(Y)_2]_bOM$ of the idealized formula IV, and optionally co-condensation products thereof, in particular organofunctional co-condensates of alkali siliconates and alkali silicates, which are preferably in the form of organofunctional alkali siloxanolates and which comprise alkali silicates, for example according to formula V shown in idealized form $MO[Si(R^1)_xY_{(y-2)-x}O]_a[Si(Y)_2]_bOM$ or formula Va shown in idealized form $MO[Si(R^1)_xY_{(y-2)-x}O]_a[Si(Y)_2]_b[Si(R^1)_xY_{(y-2)-x}O]_aOM$, where Y in formulae III, IIIa, IV, V and/or Va in each case independently $Y=O_{1/2}$ in a siloxane bond or OM, with M denoting a monovalent alkali ion, such as Na⁺ or K⁺; or ½ alkaline-earth ion, such as ½ Ca²⁺, in —ONa, —OK, or hydrogen for —OH, $R^1$ as defined, with a and b independently of one another greater than or equal to 1 and in each case independently x=1 or 2 and y=4, preferably x=1. Preferably a and b can be greater than or equal to 2, such as between 2 and 30. Moreover, both the organofunctional alkali siliconates, the alkali silicates and optionally the co-condensation products can have both linear, cyclic, branched and/or three-dimensional network structures, as they are derived from bi-, tri- and tetrafunctional hydrolysable silanes.

The invention also relates to a method in which the mixture from step 1 is supplied, for the execution of step 2, by means of a metering device, which in the simplest case has a control device, such as a shut-off device or a shut-off valve, optionally in the presence of inert gas, in particular an inert gas under pressure, preferably above from 1 bar to 10 bar, a little at a time, in particular dropwise, to a device with a delivery means, wherein the delivery means is preferably a delivery tube or hose, and the device is shielded with inert gas, in particular in the lumen with inert gas, and the end of the delivery means, in particular of the delivery tube or hose, is immersed in the alkaline solution, or, that the mixture from step 1 is transferred, for the execution of step 2, to a metering device and is shielded with inert gas, in particular with an inert gas under pressure, preferably with a pressure from 1 bar to 10 bar, the mixture from step 1 is transferred from the metering device a little at a time, in particular dropwise, to a device with a delivery means, in particular the delivery means is a delivery tube or hose, wherein the device is shielded with inert gas, and the end of the delivery means, in particular of the delivery tube or hose, is immersed in the alkaline solution. It may also be desirable if the end of the delivery means is immersed just under the surface, especially preferably it is immersed in the solution as deeply as possible.

Moreover, it is further preferred if the method is carried out in such a way that an inert gas stream, for example a nitrogen and/or argon stream, is divided and one portion of the inert gas is transferred to the metering device, in particular via the gas feed pipe, and one portion of the inert gas is transferred to the device with delivery means, in particular via the gas feed pipe. Preferably the delivery means is a delivery tube and/or hose. Preferably the inert gas stream on the two aforementioned gas feed pipes is coupled, to make the metering and process control economical.

Additionally or alternatively to one or more of the aforementioned features, it is further preferable if the mixture from step 1 is transferred by means of the metering device a little at a time to the device with the delivery means, i.e. preferably to the delivery tube, and there it is forced by the inert gas through the delivery means, in particular delivery tube, into the alkaline solution, preferably the mixture from step 1 is in each case forced dropwise directly into the solution, especially preferably the mixture from step 1 is injected by the inert gas directly into the solution, more preferably the mixture from step 1 is injected by the inert gas under pressure into the solution. Moreover, the drops are preferably in each case separated from one another by the inert gas. Additionally, the distribution and dilution of mixture 1 from step 1 at the end of the delivery means in the aqueous alkali hydroxide solution can be further supported by vigorous stirring.

The invention also relates to a solution obtainable by the method according to the invention, which has a defined alcohol content and/or which preferably has co-condensation products of organofunctional alkali siliconates with silicates. The alcohol content of the solution can preferably be between 1 ppm by weight and 25 wt. %, preferably between 10 ppm by weight and 20 wt. %, especially preferably between 100 ppm by weight and 10 wt. %, very especially preferably between 0.1 wt. % and 5 wt. %, in each case relative to the total weight of the solution. Higher amounts of alcohol can promote the solubilization of relatively long-chain organofunctional radicals $R^1$; smaller amounts of alcohol can cause a higher flashpoint of the solution.

Preferred alcohol contents in the solution comprising organofunctional alkali siliconates, silicates and optionally the co-condensation products thereof may be within the range of 10 ppm by weight and 20 wt. %, especially preferably between 100 ppm by weight and 10 wt. %, very especially preferably between 0.1 wt. % and 5 wt. %, in each case relative to the total weight of the solution. The alcohol content can also be lowered further by addition of water before processing. A solution according to the invention may optionally comprise free chlorides and optionally free alcohol, in which case, however, the organofunctional alkali siliconates and alkali silicates are essentially free of halides, such as chlorides, and are also essentially free of alkoxy groups. The same applies to any co-condensation products obtained.

The invention further relates to the use of a solution according to the invention or a solution that has been prepared by the method according to the invention for the hydrophobization of mineral building materials, in particular a solution with an alcohol content, preferably for the hydrophobization of the surface of mineral building materials or for the hydrophobization of mineral building materials in the bulk. Moreover, the use of the solution can for the hydrophobization of a portion of the mineral building material or also for the hydrophobization of the whole mineral building material, in each case comprising concrete, screed, plaster, gypsum, mortar, loam, clay, sand, ceramic, terracotta, lime sandstone, natural stone, such as sandstone, marble, granite and articles therefrom or articles containing them, such as moulded articles, comprising for example pipes, bricks, floor tiles, walls, garden tubs, roof tiles and other usual mineral building materials and articles made from these building materials, known by a person skilled in the art.

The invention likewise provides a plant, in particular for performance of a method according to the invention, which has a metering device comprising a control device, and a) the metering device comprises a first vessel with a gas feed pipe and/or a feed pipe or b) the plant comprises a metering device comprising a control device, a step 1 reactor with a feed pipe for educts and optionally a gas feed pipe for inert gas, the metering device being connected to a device which has a delivery means, delivery pipe and/or hose and a second vessel, the second vessel having a lumen and a gas feed pipe and being connected to the delivery means, in particular delivery tube or hose, the delivery means being introduced by its end into a step 2 reactor. It is sufficient when the second vessel or the lumen is suitable for enabling mixing of inert gas and the mixture from step 1, which means that the second vessel may also be a kind of expansion in the delivery means or a mixing chamber. The delivery means may also be a delivery tube, a delivery hose, a capillary or else a hollow needle. It will be clear to the person skilled in the art that the device with delivery means may also have a multitude of delivery means, for example 2 to 100, which are optionally actuated by means of control devices.

It may also be preferable when, in the plant, the mixture from step 1 can be transferred with the control device, either from the first vessel or the step 1 reactor, in a defined manner into the lumen of the second vessel, and can be introduced into the solution via the delivery means, the delivery means preferably being a delivery tube or hose, the end of which is immersed into the alkali hydroxide solution in the step 2 reactor by means of the inert gas supplied via the gas feed pipe, and more particularly can be injected into the solution. The length of the delivery means is preferably such that the end is immersed well into the solution, it being especially preferable that the end is immersed into the solution as deeply as possible.

According to the invention, it is sufficient when the second vessel has a lumen which allows the mixture from step 1 to be introduced or transferred a little at a time, preferably dropwise, into the delivery means in the presence of an inert gas, such that the individual portions or droplets can be forced or injected into the solution in the step 2 reactor essentially separated by the inert gas. It may therefore be sufficient when the second vessel represents merely a kind of expansion in the delivery means with gas feed pipe.

The following examples explain the method according to the invention and the equipment according to the invention in more detail, without limiting the invention to these examples.

EXAMPLE 1

Preparation of an 8% Aqueous Solution of K-Propylsiliconate and K-Silicate 100 g of a 1:1 mixture (based on the molar composition) of propyltrichlorosilane and tetrachlorosilane was put in a 250-ml round-bottomed flask with dropping funnel and gas offtake tube. 10 g ethanol was added slowly, stirring vigorously. The temperature rose during addition, but was not to exceed 60° C. It was cooled down if necessary. After all of the ethanol had been added, it was stirred for a further 10 min and the mixture obtained was used further directly.

300 g of 40% aqueous KOH was put in a 500 ml round-bottomed flask (5) with gas delivery tube (2.2) without frit. 50 g of the product from the first reaction step was put in a dropping funnel (1) with $N_2$ connection (1.4). The product was now added slowly, stirring vigorously, via the gas delivery tube (2.2) to the aqueous lye (4). The $N_2$-stream is divided so that one portion exerts pressure on the contents of the dropping funnel (1), and the other portion flows round the opening of the dropping funnel (1.1 in 3 of device 2). The two streams are combined again in the gas delivery tube (2.2). During addition, the temperature rose. Were it to rise above 60° C., it was to be cooled down. After complete addition, stirring was continued until a clear solution was obtained.

$^{29}$Si-NMR (100 MHz, $D_2O$): δ=−46 ($CH_3CH_2CH_2Si(O^-)_3$), −71 ($Si(O^-)_4$).

EXAMPLE 2

Preparation of an 11% Aqueous Solution of K-Propylsiliconate and K-Silicate 100 g of a 1:1 mixture (based on the molar composition) of propyltrichlorosilane and tetrachlorosilane was put in a 250 ml round-bottomed flask with dropping funnel and gas offtake tube. 10 g ethanol was added slowly, stirring vigorously. The temperature rose during addition, but was not to exceed 60° C. It was cooled down if necessary. After all of the ethanol had been added, it was stirred for a further 10 min and the mixture obtained was used further directly.

440 g of 50% aqueous KOH was put in a 500 ml round-bottomed flask (5) with gas delivery tube (2.2) without frit. 100 g of the product from the first reaction step was put in a dropping funnel (1) with $N_2$ connection (1.4). The product was now added slowly, stirring vigorously, via the gas delivery tube (1.4) to the aqueous lye (4). The $N_2$-stream was divided so that one portion (1.4) exerts pressure on the contents of the dropping funnel (1), and the other portion (2.5) flows round the opening of the dropping funnel (1.1 in 3 of device 2). The two streams were combined again in the gas delivery tube (2.2). During addition, the temperature rose. If it was over 60° C., it was cooled down. After complete addition, stirring was continued until a clear solution was obtained.

$^{29}$Si—NMR (100 MHz, $D_2O$): δ=−45.6 ($CH_3CH_2CH_2Si(O^-)_3$), −70.5 ($Si(O^-)_4$).

3. COMPARATIVE EXAMPLE

Preparation of an 8% Aqueous Solution of K-Propylsiliconate and K-Silicate 100 g of a 1:1 mixture (based on the molar composition) of propyltrichlorosilane and tetrachlorosilane was put in a 250 ml round-bottomed flask with dropping funnel and gas offtake tube. 10 g ethanol was added slowly, stirring vigorously. The temperature rose during addition. However, it was not to exceed 60° C. It was cooled down if necessary. After all of the ethanol had been added, it was stirred for a further 10 min and the mixture obtained was used further directly.

300 g of 40% aqueous KOH was put in a 500 ml round-bottomed flask with gas delivery tube (2.2) without frit. 50 g of the product from the first reaction step was put in a dropping funnel (1) without $N_2$ connection. The product was now added slowly, stirring vigorously, via the gas delivery tube (2.2) to the aqueous lye. Addition had to be stopped after just a few milliliters, as the feed lines became clogged.

4. COMPARATIVE EXAMPLE

Methylsiliconate solution, 34%

Tests of the Reaction Products from Example 1

The reaction produces from Example 1 were used without further purification or dilution. Massive brick cubes from Poroton solid brick with an edge length of 50 mm and concrete cubes made of concrete to DIN EN 1045 with an edge length of 50 mm were conditioned at 25° C. and 60% humidity for 24 h and then immersed for 5 s in the solutions from Examples 1 and 2. Adhering moisture was removed by lightly dabbing the surfaces with a paper cloth. Then the treated test specimens were stored at 25° C. and 60% humidity for 14 days, in such a way that air could reach all sides. The reduction of water absorption was determined on these specimens on the basis of DIN EN 13580.

The percentage reduction was calculated by comparing with an untreated specimen of the same type (Table 1a). The following Table 1a shows amounts used and reduction of water absorption of different materials.

TABLE 1a

Reduction in water absorption by brick and concrete.

| Substrate | Amount applied [g/m²] | Reduction in water absorption [%] |
|---|---|---|
| Brick | 313 | 89.2 |
| Concrete | 167 | 82.5 |

In addition, bricks as specimens were treated with a solution from Example 1 and with a methylsiliconate solution (4. Comparative example) as described above. This was followed by storage in KOH. Table 1a which follows shows amounts used and reduction in water absorption of different materials.

TABLE 1b

Reduction in water absorption by brick, Ex. 1 and methylsiliconate.

| On brick | Amount applied [g/m²] | Reduction in water absorption [%] | Reduction in water absorption [%] after storage in KOH[1] | Penetration depth [mm] |
|---|---|---|---|---|
| Ex. 1 | 313 | 89.2 | 68.1 | 1.5-2.6 |
| 4. Comparative example | 307 | 84 | 7.1 | 2-2.5 |

[1]Storage in KOH, 24 h in analogy to DIN EN 13580.

Testing of the Reaction Products from Example 2

Cylindrical gypsum specimens composed of a commercial gypsum from Knauf with a water:gypsum ratio of 0.5 were produced. 3 w % (rel. to the gypsum powder) of the reaction product from Example 2 were added to the aqueous gypsum slurry. The gypsum specimens had a diameter of 50 mm and a height of 25 mm and were poured into PE moulds. The gypsum specimens were cured at 25° C. and 60% rel. humidity for 28 days; after 2 days under these conditions, they were removed from the moulds, then stored in such a way that air was able to circulate freely from all sides. The water absorption was determined based on DIN EN 520; the results can be found in Table 2 below.

TABLE 2

Water absorption by gypsum specimens.

| Specimen | Water absorption [%] |
|---|---|
| Untreated reference | 23.8 |
| Gypsum specimen + 3 w % of product from Example 2 | 11.8 (H3 class) |

Working Example of Plant

Figure 1:
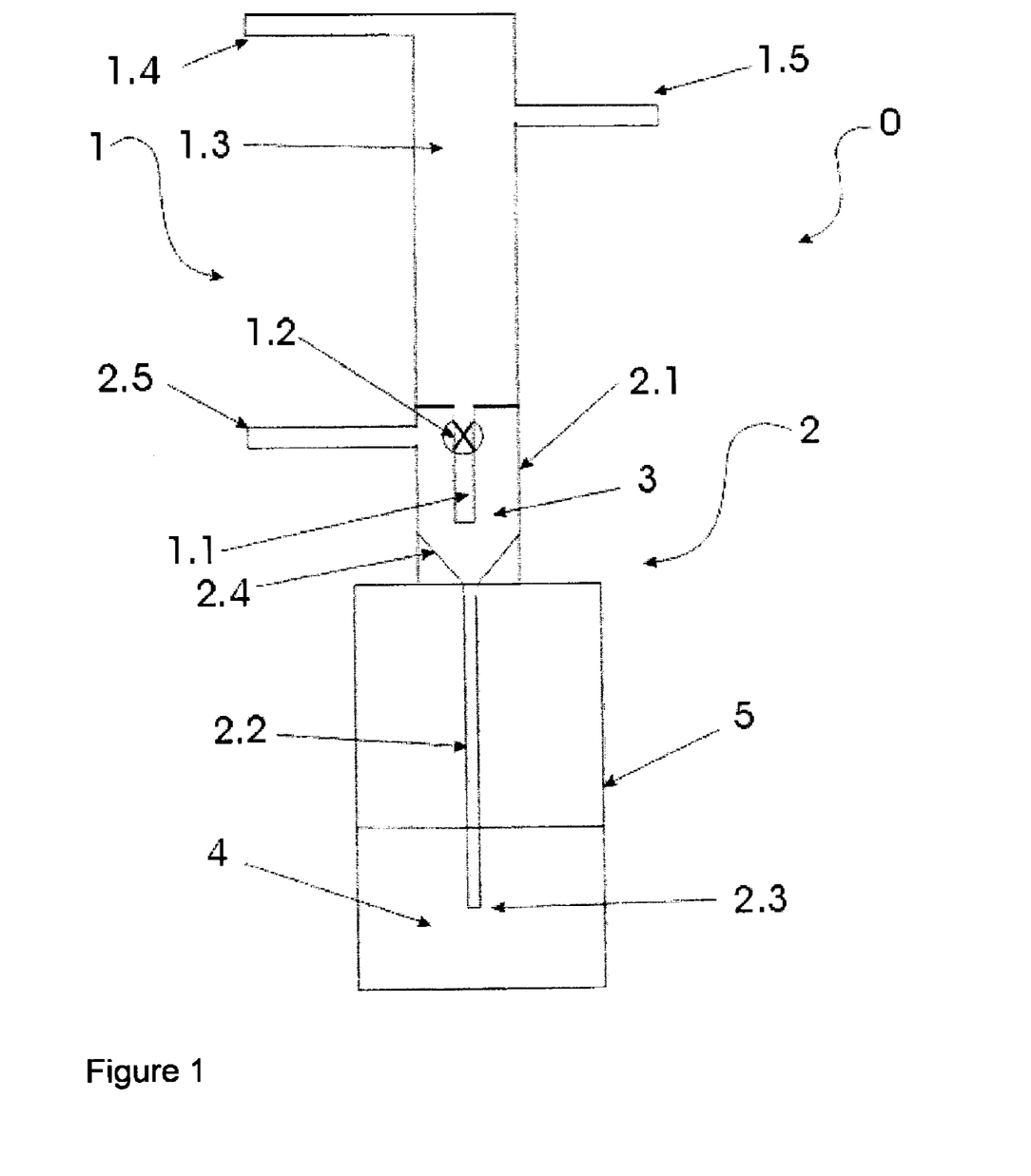
FIG. 1 illustrates a plant with a metering device and a device with delivery means, the delivery means being a delivery tube.

FIG. 1 shows a plant 0 according to the invention for carrying out the method according to the invention, with a metering device 1 and a control device 1.2, which permits the metering of the mixture from step 1 a little at a time into the delivery means 2.2. The metering device 1 can also comprise a) a first vessel 1.3 with a gas feed pipe 1.4 and/or a feed pipe (1.5, as shown in FIG. 1 or b) the plant comprises a metering device 2 (FIG. 2) with control device 1.2 and comprises a step 1 reactor (7) with a feed pipe for educts 8 and optionally a feed pipe for inert gas 6. The metering device 1 is connected to a device 2, which has a delivery means 2.2, which can usually be a delivery tube 2.2 or a delivery hose 2.2. In addition, the device 2 has a so-called second vessel 2.1, whose purpose, which is a kind of mixing chamber of inert gas and portions or drops of the mixture from step 1. For this, the second vessel 2.1 has a lumen 3 and a gas feed pipe 2.5 and is connected to the delivery means 2.2, in particular delivery tube or hose 2.2, wherein the end 2.3 of the delivery means is led into a step 2 reactor (5). Moreover, the length of the delivery means is such that the end 2.3 is immersed in the solution 4. Preferably the end is immersed in the solution 4 as deeply as possible.

Figure 2:
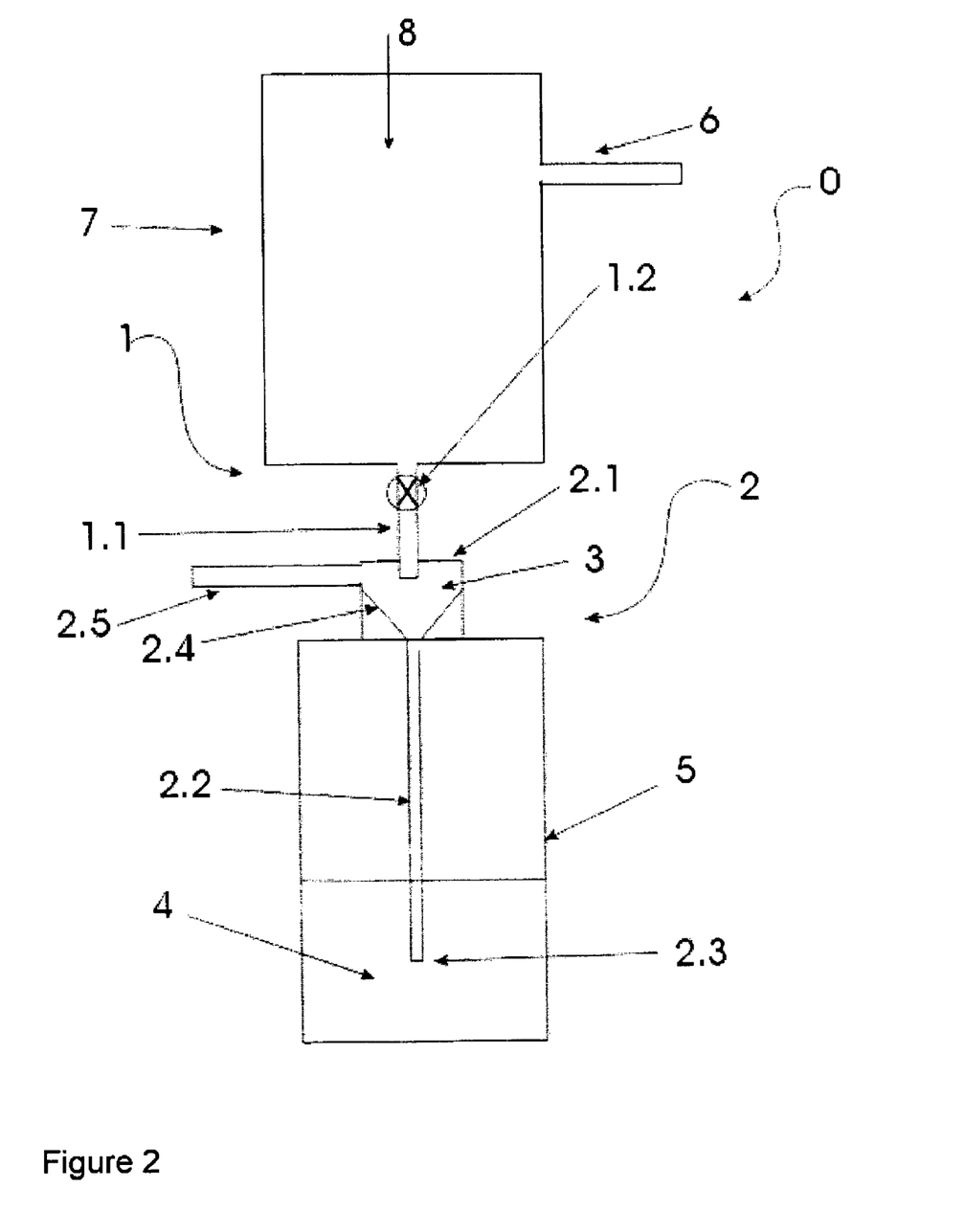
FIG. 2 illustrates a plant comprising a reactor step 1 and a metering device with a control device and feed pipe 1.1 and a device with a delivery tube in reactor step 2.

In FIGS. 1 and 2 it is shown schematically that a plant 0 according to the invention is to be suitable for transferring the mixture from step 1 with a control device 1.2, which is optionally connected to the first vessel 1.3 or the step 1 reactor (7), preferably by means of a feed pipe 1.1, defined in the lumen 3 of the second vessel 2.1. There, the mixture from step 1 is shielded with inert gas and the individual drops are virtually separated by the inert gas. It is therefore important that the delivery means preferably has a diameter or is such that a coalescence of the portions or drops in the delivery means itself is prevented in continuous metering. In addition, a gas feed pipe 2.5 is connected to the vessel 2.1. The vessel 2.1 can have a kind of collecting device 2.4 for example of the nature of a funnel, which is located above the delivery means 2.2. The delivery means is preferably a rigid tube or a capillary 2.2, the bottom end of which 2.3 is introduced into the reactor 5 so far that the end 2.3 is immersed in the solution 4 during execution of the method. Moreover, the second vessel 2.1 can have a lumen 3, which makes it possible to introduce the mixture from step 1 for example dropwise in the presence of nitrogen into the delivery tube separately and inject it directly into the solution in the reactor of step 2. It can therefore be sufficient if the second vessel 2.1 represents a kind of expansion in the delivery means 2.2 with gas feed pipe 2.5.

The invention claimed is:

1. A method of preparing a solution comprising an organofunctional alkali siliconate, an organofunctional alkali silicate and optionally a co-condensation product thereof, the method comprising:
   preparing a mixture comprising an organofunctional silane of the formula I:

$(R^1)_x SiHal_{(y-x)}$     (I), with a halosilane of the formula II:

$Si(Hal)_4$     (II), an alcohol, and optionally water, to obtain a reacted mixture,
   wherein
   $R^1$ is independently an organofunctional residue,
   Hal is a hydrolysable residue, which is independently chlorine or bromine,
   x is 1 or 2, and
   y is 4; and
   introducing the reacted mixture in the presence of an inert gas into an aqueous alkali hydroxide solution, wherein the inert gas is supplied so that it introduces a portion of the reacted mixture directly into the aqueous alkaline solution.

2. The method according to claim 1, further comprising stirring vigorously the mixture in the preparing, the solution in the introducing, or both.

3. The method according to claim 1, wherein the organofunctional radical $R^1$ each independently comprises 1 to 18 carbon atoms.

4. The method according to claim 1, wherein a solution comprising the organofunctional alkali siliconate, the organofunctional alkali silicate and optionally a co-condensation product thereof is obtained in the introducing.

5. The method according to claim 1, wherein the organofunctional silane of the formula I and the halosilane of the formula II have a molar ratio of from 0.5:10 to 10:0.5.

6. The method according to claim 1, wherein the alcohol is added in a ratio of from 1 to 100 mol. % relative to the hydrolysable residue in mol.

7. The method according to claim 1, wherein the mixture from the preparing is introduced immediately into an aqueous, alkaline solution and is reacted to a solution comprising an organofunctional siliconate, an organofunctional silicate and optionally a co-condensation product thereof.

8. The method according to claim 1, wherein the temperature in the preparing, the introducing, or both, does not exceed 80° C.

9. The method according to claim 4, wherein the alcohol is removed from the solution comprising the organofunctional alkali siliconate, the organofunctional alkali silicate and optionally co-condensation product thereof.

10. The method according to claim 7, wherein a proportion of the organofunctional siliconate, organofunctional silicate and co-condensation product thereof in the solution is between 1 and 40 wt. %, relative to a total weight of the solution, wherein a content is optionally adjusted by adding water.

11. The method according claim 1, wherein the alcohol comprises at least one selected from the group consisting of ethanol, methanol, and propanol, and an alcohol content in the solution is between 1 ppm by weight and 25% by weight, based on a total weight of the solution.

12. The method according to claim 1, wherein the inert gas comprises nitrogen, argon, or both, or further gases which do not react with the mixture, the solution, or both.

13. The method according to claim 1, wherein the portion of the mixture from the preparing is supplied to the introducing by means of a metering device, in the presence of inert gas, to a device which has a delivery means and is blanketed with inert gas, an end of which is immersed into the alkaline solution, or the mixture from the preparing is transferred into a metering device and is blanketed with inert gas, in which the portion of the mixture is introduced from the metering device to a device which has delivery means and is blanketed with inert gas, an end of which is immersed into the alkaline solution.

14. The method according to claim 13, wherein an inert gas stream is divided and a portion of the inert gas stream is transferred into the metering device and another portion of the inert gas stream into the device with delivery means.

15. The method according to claim 13, wherein the portion of the mixture from the preparing is transferred by means of a metering device into a device with a delivery means and there it is forced by means of the inert gas through the delivery means into the alkaline solution.

16. The method according to claim 1, wherein the organofunctional radical $R^1$ each independently comprises a linear, branched or cyclic alkyl radical having 1 to 18 carbon atoms, an alkylene radical having 1 to 18 carbon atoms, an aryl radical having 6, 10, 12 or 13 carbon atoms, or an alkylaryl or arylalkyl radical having 7 to 18 carbon atoms.

* * * * *